(12) United States Patent
Goldman et al.

(10) Patent No.: US 7,829,332 B2
(45) Date of Patent: Nov. 9, 2010

(54) PURINES ARE SELF-RENEWAL SIGNALS FOR NEURAL STEM CELLS, AND PURINE RECEPTOR ANTAGONISTS PROMOTE NEURONAL AND GLIAL DIFFERENTIATION THEREFROM

(75) Inventors: Steven A. Goldman, Webster, NY (US); Maiken Nedergaard, Webster, NY (US); Jane Lin, Larchmont, NY (US)

(73) Assignees: Cornell Research Foundation, Inc., Ithaca, NY (US); New York Medical College, Valhalla, NY (US)

( * ) Notice: Subject to any disclaimer, the term of this patent is extended or adjusted under 35 U.S.C. 154(b) by 569 days.

(21) Appl. No.: 11/054,919

(22) Filed: Feb. 10, 2005

(65) Prior Publication Data
US 2005/0181503 A1  Aug. 18, 2005

Related U.S. Application Data

(60) Provisional application No. 60/544,503, filed on Feb. 13, 2004.

(51) Int. Cl.
*C12N 5/06* (2006.01)
(52) U.S. Cl. ........................ 435/375; 435/376; 435/377; 435/384
(58) Field of Classification Search ........................ None
See application file for complete search history.

(56) References Cited

U.S. PATENT DOCUMENTS

| | | | |
|---|---|---|---|
| 5,753,506 A | 5/1998 | Johe | |
| 5,827,740 A | 10/1998 | Pittenger | |
| 6,326,390 B1 | 8/1999 | Leung et al. | |
| 5,968,829 A | 10/1999 | Carpenter | |
| 5,980,885 A | 11/1999 | Weiss et al. | |
| 6,001,654 A | 12/1999 | Anderson et al. | |
| 6,033,906 A | 3/2000 | Anderson | |
| 6,238,922 B1 | 5/2001 | Uchida | |
| 6,294,346 B1 | 9/2001 | Weiss et al. | |
| 6,322,784 B1 | 11/2001 | Pittenger et al. | |
| 6,432,711 B1 | 8/2002 | Dinsmore et al. | |
| 6,528,245 B2 | 3/2003 | Sanchez-Ramos et al. | |
| 2002/0009743 A1 | 1/2002 | Carpenter | |
| 2002/0019046 A1 | 2/2002 | Carpenter et al. | |
| 2002/0064873 A1 | 5/2002 | Yang et al. | |
| 2002/0090723 A1 | 7/2002 | Carpenter et al. | |
| 2002/0091133 A1 | 7/2002 | Taylor | |
| 2002/0094571 A1 | 7/2002 | Weiss et al. | |
| 2002/0098585 A1 | 7/2002 | Weiss et al. | |
| 2002/0165213 A1 | 11/2002 | Weiss et al. | |
| 2002/0197238 A1 | 12/2002 | Weiss et al. | |
| 2003/0003090 A1 | 1/2003 | Prockop et al. | |
| 2003/0013192 A1 | 1/2003 | Laeng et al. | |
| 2003/0036195 A1 | 2/2003 | Studer et al. | |
| 2003/0049837 A1 | 3/2003 | Weiss et al. | |
| 2003/0049838 A1 | 3/2003 | Thompson et al. | |
| 2003/0054551 A1 | 3/2003 | Shingo et al. | |
| 2003/0054998 A1 | 3/2003 | Shingo et al. | |
| 2003/0068819 A1 | 4/2003 | Zhang et al. | |
| 2003/0082802 A1 | 5/2003 | Rajan et al. | |
| 2003/0095956 A1 | 5/2003 | Weiss et al. | |
| 2003/0118566 A1 | 6/2003 | Neuman et al. | |

OTHER PUBLICATIONS

Lin et al. *Develop. Biol.*, vol. 302, pp. 356-366, 2007.*
Scemes et al. *J. Neurosci.*, vol. 23, pp. 11444-11452, 2003.*
Schwiebert, *Clin. Experim. Pharmacol. Physiol.*, vol. 28, 2001, pp. 340-350.*
Kearns et al., *Experim. Neurol.*, vol. 182, 2003, pp. 240-244.*
Arcuino et al., "Intercellular Calcium Signaling Mediated by Point-Source Burst Release of STP," *Proc. Natl. Acad. Sci. USA* 99:9840-9845 (2002).
Aubert et al., "Functional Gene Screening in Embryonic Stem Cells Implicates Wnt Antagonism in Neural Differentiation," *Nat. Biotechnol.* 20:1240-1245 (2002).
Braun et al., "Expression of the Ecto-ATPase NTPDase2 in the Germinal Zones of the Developing and Adult Rat Brain," *Eur. J. Neurosci.* 17:1355-1364 (2003).
Burnstock, G., "Potential Therapeutic Targets in the Rapidly Expanding Field of Purinergic Signalling," *Clin. Med.* 2:45-53(2002).
Burnstock, G., "Purinergic Signaling and Vascular Cell Proliferation and Death," *Arterioscler Thromb. Vasc. Biol.* 22:364-373 (2002).
Cotrina et al., "Connexins Regulate Calcium Signaling by Controlling ATP Release," *Proc. Natl. Acad. Sci. USA* 95:15735-15740 (1998).
Cotrina et al., "Cytoskeletal Assembly and ATP Release Regulate Astrocytic Calcium Signaling," *J. Neurosci.* 18:8794-8804 (1998).
Deptala et al., "Differences in Induction of p53, p21WAF1 and Apoptosis in Relation to Cell Cycle Phase of MCF-7 Cells Treated with Camptothecin," *Int. J. Oncol.* 15:861-871 (1999).
Dixon et al., "Extracellular Nucleotides Stimulate Proliferation in MCF-7 Breast CancerCells via P2-Purinoceptors," *Br. J. Cancer* 75:34-39 (1997).
Gage, F., "Mammalian Neural Stem Cells," *Science* 287:1433-1438 (2000).

(Continued)

*Primary Examiner*—Jeffrey Stucker
*Assistant Examiner*—Stephen Gucker
(74) *Attorney, Agent, or Firm*—Nixon Peabody LLP

(57) ABSTRACT

The present invention relates to a method of inhibiting differentiation of a population of neural stem cells by contacting a purinergic receptor agonist and a population of neural stem cells under conditions effective to inhibit differentiation of the population of neural stem cells. Another aspect of the present invention relates to a method of producing neurons and/or glial cells from a population of neural stem cells by culturing a population of neural stem cells with a purinergic receptor antagonist under conditions effective to cause the neural stem cells to differentiate into neurons and/or glial cells. The purinergic receptor agonist can also be used in a method of inducing proliferation and self-renewal of neural stem cells in a subject and a method of treating a neurological disease or neurodegenerative condition in a subject. The purinergic receptor antagonist can also be used in treating a neoplastic disease of the brain or spinal cord in a subject.

5 Claims, 5 Drawing Sheets

OTHER PUBLICATIONS

Goldman et al., "In vitro Neurogenesis by Neuronal Precursor Cells Derived from the Adult Songbird Brain," *J. Neurosci.* 12:2532-2541 (1992).

Keyoung et al., "High-Yield Selection and Extraction of Two Promoter-Defined Phenotypes of Neural Stem Cells from the Fetal Human Brain," *Nat. Biotechnol.* 19:843-850 (2001).

Laywell et al., "Identification of a Multipotent Astrocytic Stem Cell in the Immature and Adult Mouse Brain," *Proc. Natl. Acad. Sci USA* 97:13883-13338 (2000).

Lim et al., "Noggin Antagonizes BMP Signaling to Create a Niche for Adult Neurogenesis," *Neuron* 28:713-726 (2000).

Maclaughlin et al., "Adenosine Activates Mesangial Cell Proliferation," *Cell Signal* 9:59-63 (1997).

Mckay, R. D., "The Origins of Cellular Diversity in the Mammalian Central Nervous System," *Cell* 58:815-821 (1989).

Mckay, R., "Stem Cells in the Central Nervous System," *Science* 276:66-71 (1997).

Merighi et al., "Adenosine Receptors as Mediators of Both Cell Proliferation and Cell Death of Cultured Human Melanoma Cells," *J. Invest. Dermatol.* 119:923-933 (2002).

Michoud et al., "Effects of Extracellular Triphosphate Nucleotides and Nucleosides on Airway Smooth Muscle Cell Proliferation," *Am. J. Respir. Cell Mol. Biol.* 27:732-738 (2002).

Morshead et al., "Neural Stem Cells in the Adult Mammalian Forebrain: A Relatively Quiescent Subpopulation of Subependymal Cells," *Neuron* 13:1071-1082 (1994).

Nedergaard, M., "Direct Signaling from Astrocytes to Neurons in Cultures of Mammalian Brain Cells," *Science* 263:1768-1771 (1994).

Ourednik et al., "Neural Stem Cells—A Versatile Tool for Cell Replacement and Gene Therapy in the Central Nervous System," *Clin. Genet.* 56:267-278 (1999).

Rees et al., "adenosine-Regulated Cell Proliferation in Pituitary Folliculostellate and Endocrine Cells: Differential Roles for the $A_1$ and $A_{2B}$ Adenosine Receptors," *Endocrinology* 143:2427-2436 (2002).

Reynolds et al., "A Multipotent EGF-Responsive Striatal Embryonic Progenitor Cell Produces Neurons and Astrocytes," *J. Neurosci.* 12:4565-4574 (1992).

Reynolds et al., "Generation of Neurons and Astrocytes from Isolated Cells of the Adult Mammalian Central Nervous System," *Science* 255:1707-1710 (1992).

Sanches et al., "ATP Induces Proliferation of Retinal Cells in Culture via Activation of PKC and Extracellular Signal-Regulated Kinase Cascade," *Int. J. Dev. Neurosci.* 20:21-27 (2002).

Sauer et al., "The DC Electrical-Field-Induced Ca2+ Response and Growth Stimulation of Multicellular Tumor Spheroids are Mediated by ATP Release and Purinergic Receptor Stimulation," *J. Cell. Sci.* 115:3265-3273 (2002).

Seaberg et al., "Stem and Progenitor Cells: The Premature Desertion of Rigorous Definitions," *Trends Neurosci.* 26(3):125-131 (2003).

Stevens et al., "Response of Schwann Cells to Action Potentials in Development," *Science* 287:2267-2271 (2000).

Takano et al., "Suramin Inhibits Glioma Cell Proliferation In vitro and in the Brain," *J. Neurooncol.* 21:189-201 (1994).

Taupin et al., "FGF-2-Responsive Neural Stem Cell Proliferation Requires CCg, A Novel Autocrine/Paracrine Cofactor," *Neuron* 28:385-397 (2000).

Tu et al., "$P2Y_2$ Receptor-Mediated Proliferation of $C_6$ Glioma Cells via Activation of Ras/Raf/MEK/MAPK Pathway," *Br. J. Pharmacol.* 129:1481-1489 (2000).

Uchida et al., "Direct Isolation of Human Central Nervous System Stem Cells," *Proc. Natl. Acad. Sci. USA* 97:14720-14725 (2000).

Wang et al., "Extracellular ATP and ADP Stimulate Proliferation of Porcine Aortic Smooth Muscle Cells," *J. Cell Physiol.* 153:221-233 (1992).

Wechsler-Reya et al., "Control of Neuronal Precursor Proliferation in the Cerebellum by Sonic Hedgehog," *Neuron* 22:103-114 (1999).

Weiss et al., "Is There a Neural Stem Cell in the Mammalian Forebrain?" *Trends Neurosci.* 19:387-393 (1996).

Kittner et al., "Stimulation of P2YI Receptors Causes Anxiolytic-Like Effects In The Rat Elevated Plus Maze: Implications For The Involvement of P2YI Receptor-Mediated Nitric Oxide Production," Neuropsychopharmacology, 28:435-444 (2003).

Kim et al., "Adenosine Receptor Blockade Reverses Hypophagia And Enhances Locomotor Activity Of Dopamine-Deficient Mice," PNAS, 100:1346-1351 (2003).

Blum et al., "The Adenosine A1 Receptor Agonist Amine Congener Exerts A Neurprotective Effect Against The Development Of Striatal Lesions And Motor Impairments In The 3-Nitropropionic Acid Model Of Neurotoxicity," The Journal of Neuroscience, 22:9122-9133 (2002).

Van Der Weyden et al., "Signal Transduction and White Cell Maturation Via Extracellular ATP and the P2Y11 Receptor," Immunology and Cell Biology 78:369-374 (2000).

Ryu et al., "Adenosine Triphosphate Induces Proliferation of Human Neural Stem Cells: Role of Calcium and p70 Ribosomal Protein S6 Kinase," Journal of Neuroscience Research 72:352-362 (2003).

Abbracchio et al., "International Union of Pharmacology LVIII: Update on the P2Y G Protein-Coupled Nucleotide Receptors: From Molecular Mechanisms and Pathophysiology to Therapy," Pharmacol Rev 58:281-341 (2006).

King et al., "Purinergic Receptors," In: Undertanding G Protein-Coupled Receptors and Their Role in the CNS, Eds. M. Pangalos and C. Davies, Oxford University Press, Oxford, pp. 422-438 (2002).

\* cited by examiner

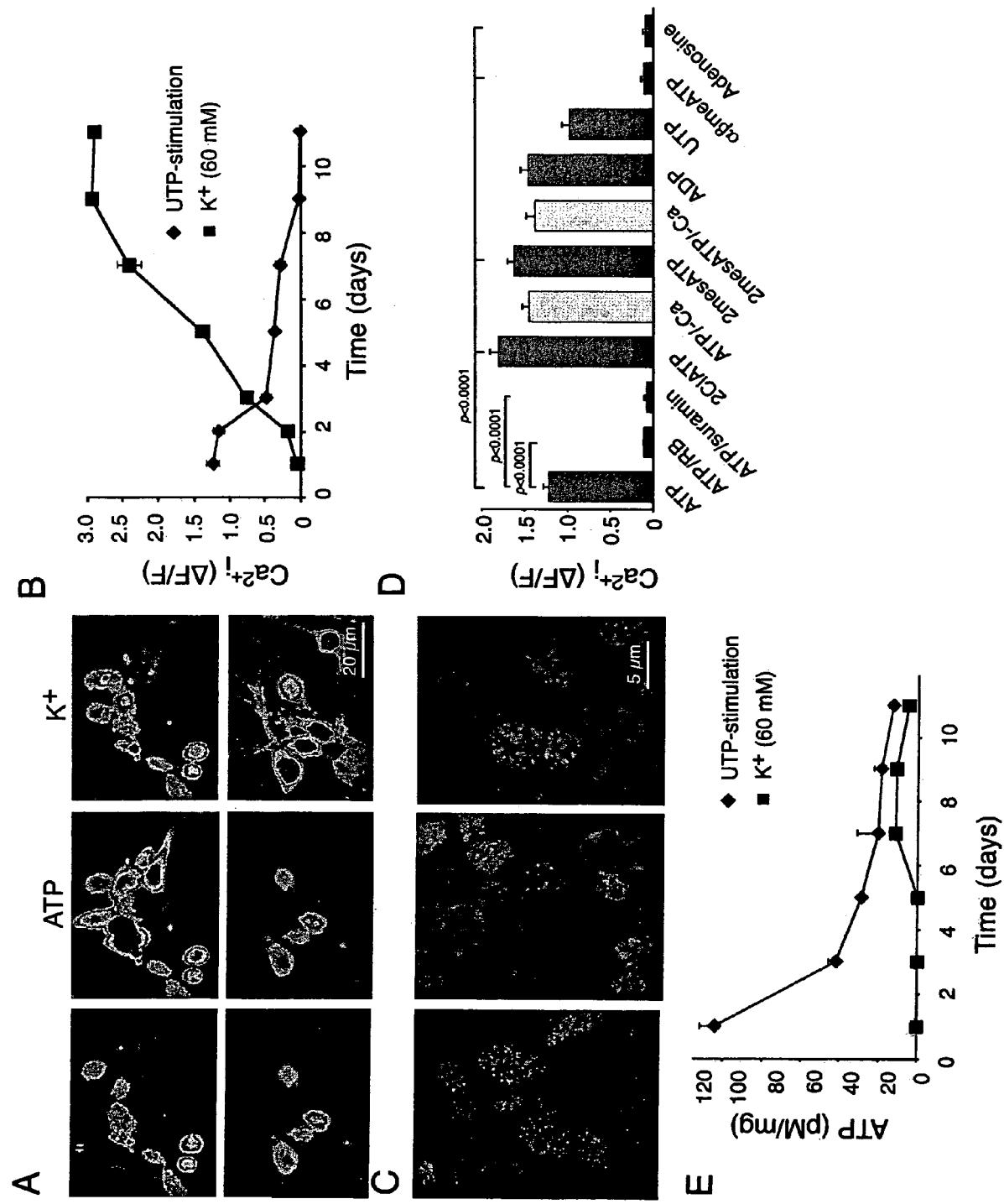
Figures 1A-E

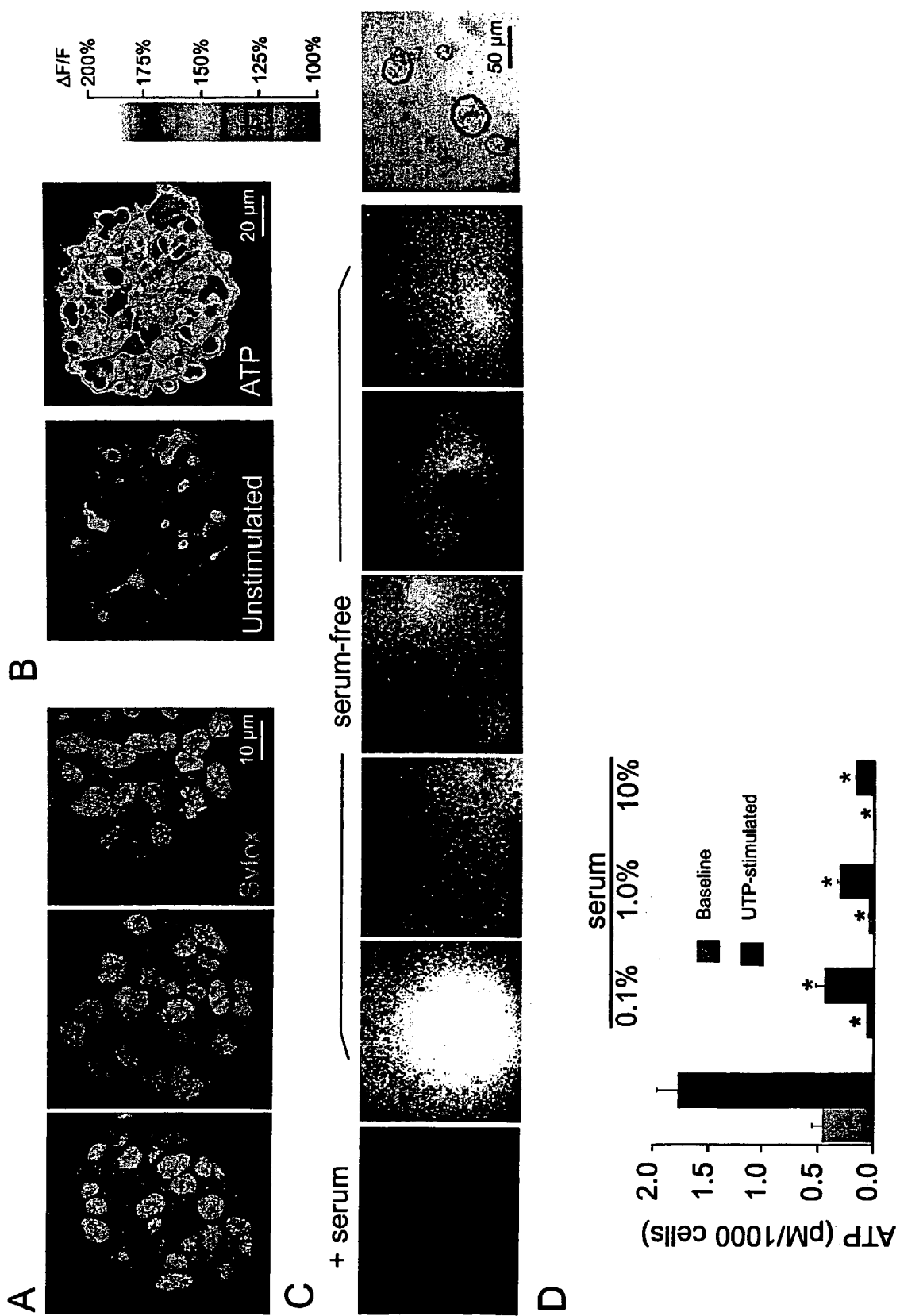
Figures 2A-D

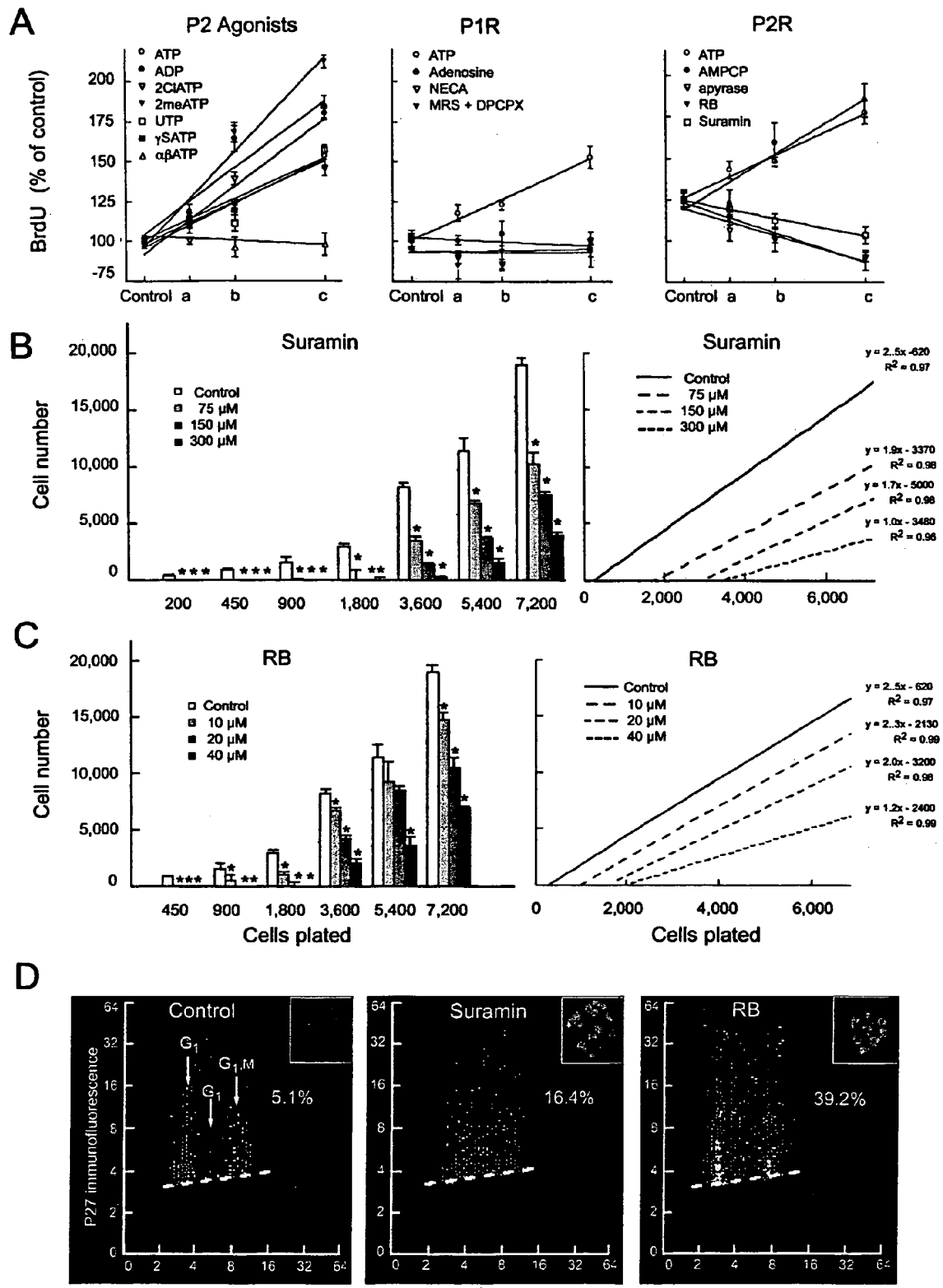
Figures 3A-D

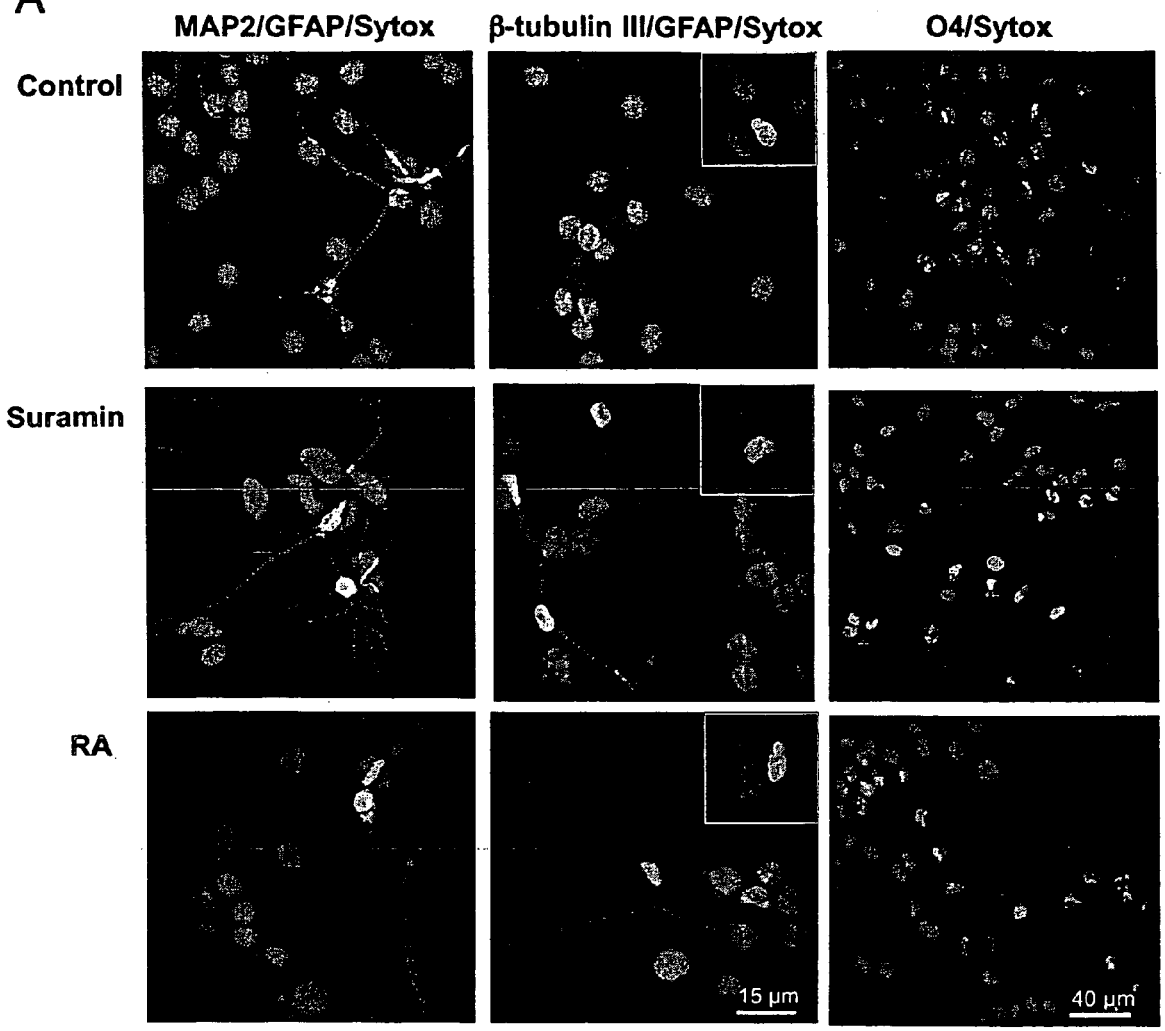
Figures 4A-B

A  P2Y2/Nestin/Sytox
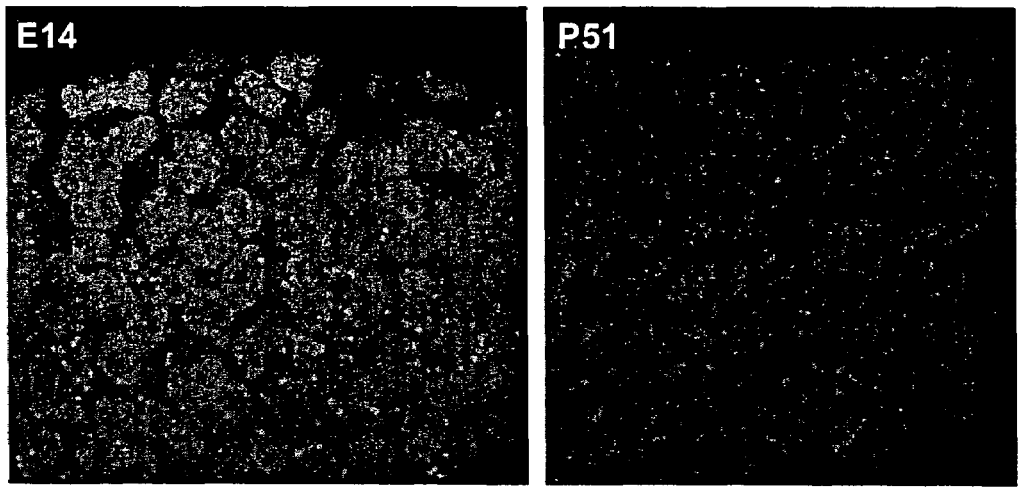
B  Ectonucleotidase activity
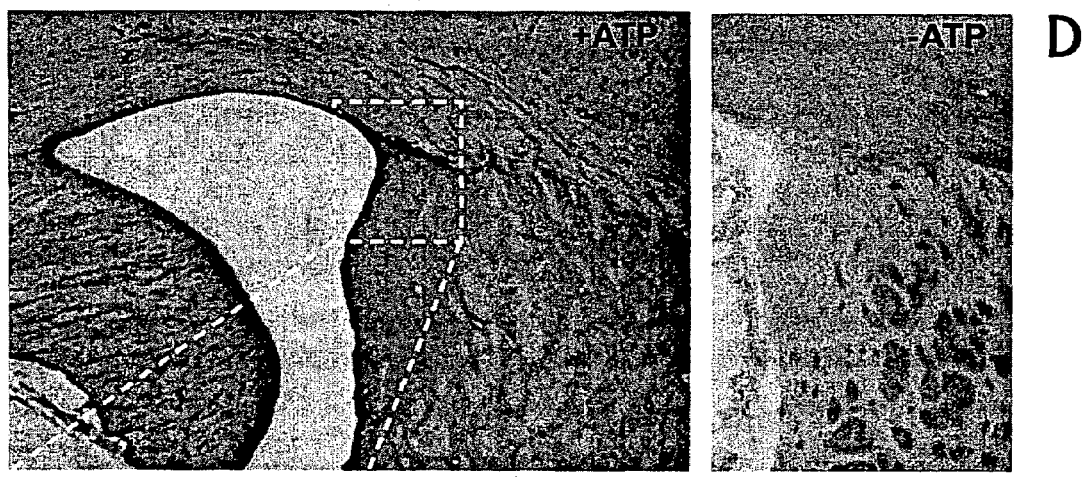
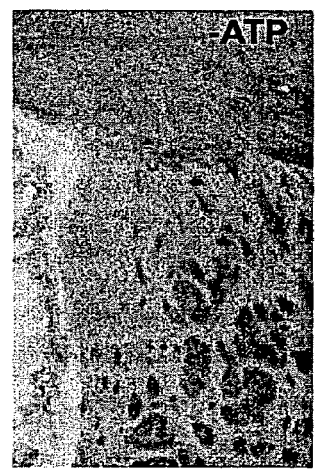 D
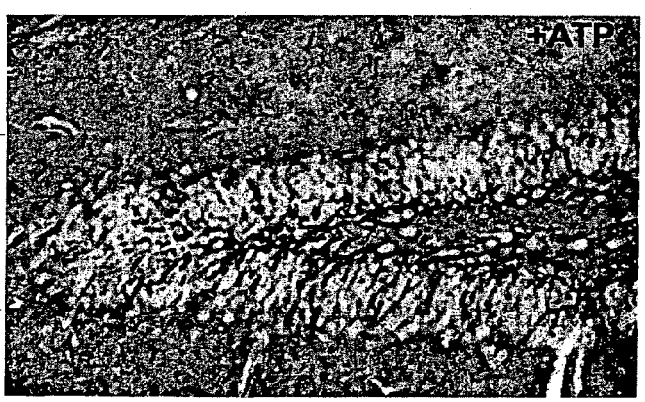 E
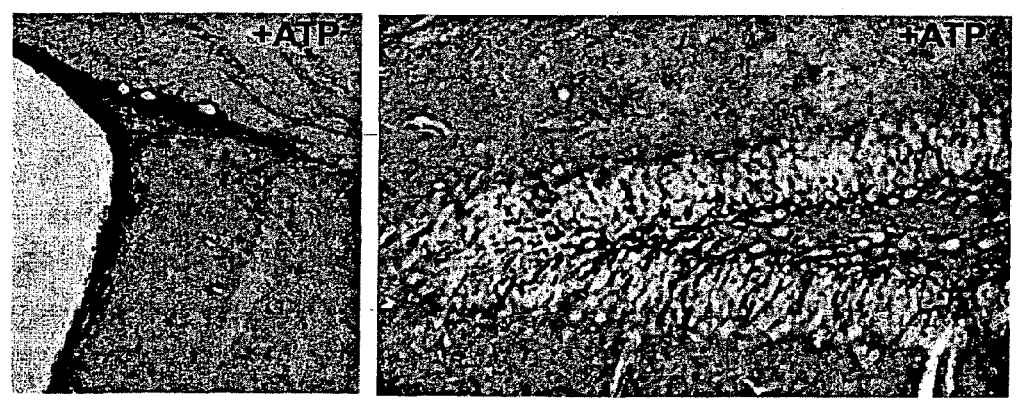
Figures 5A-E

PURINES ARE SELF-RENEWAL SIGNALS FOR NEURAL STEM CELLS, AND PURINE RECEPTOR ANTAGONISTS PROMOTE NEURONAL AND GLIAL DIFFERENTIATION THEREFROM This application claims benefit of U.S. Provisional Patent Application Ser. No. 60/544,503, filed Feb. 13, 2004.

The subject matter of this application was made with support from the United States Government under National Institutes of Health Grant Nos. NS33106 and NS38073. The United States Government may have certain rights.

FIELD OF THE INVENTION

The present invention relates to methods of inhibiting differentiation of a population of neural stem cells, producing neurons and/or glial cells from a population of neural stem cells, inducing proliferation and self-renewal of neural stem cells in a subject, treating a neurological disease or neurodegenerative condition in a subject, and treating a neoplastic disease of the brain or spinal cord in a subject.

BACKGROUND OF THE INVENTION

Neural stem cells are self-renewing multipotential progenitor cells, whose daughter cells can differentiate into both neurons and glia (Gage, F., Science 287:1433-1438 (2000); McKay, R. D., Cell 58:815-21 (1989); McKay, R., Science 276:66-71 (1997); Weiss et al., Trends Neurosci 19:387-93 (1996); Ourednik et al., Clin Genet 56:267-78 (1999)). An important feature of neural stem cells is their ability to replicate themselves by symmetric division and clonal expansion, but no humoral agents have yet been defined that specifically support these self-renewing divisions. Mitogens, including EGF and FGF, support the continued proliferation and expansion of neural stem cells, though cofactors appear to be required for low density culture (Taupin et al., Neuron 28:385-397 (2000)). Neural stem cells have proven particularly amenable to growth as free-floating clusters in suspension culture, designated neurospheres by Weiss and colleagues (Morshead et al., Neuron 13:1071-82 (1994); Reynolds et al., J Neurosci 12:4565-74 (1992); Reynolds et al., Science 255:1707-10 (1992); Laywell et al., Proc Natl Acad Sci USA 97:13883-8 (2000)), following their observation that the attachment of neural stem cells may result in the loss of their capacity for self-renewal. Even in the presence of mitogens, neural stem cells typically differentiate into committed progenitors and their neuronal and glial progeny when raised in monolayer cultures. The need for being in close contact with one another may indicate that a short-range autocrine/paracrine signaling mechanism is required for continued expansion of neural stem cells. The close-acting wnt/frizzled pathway has been implicated in the suppression of neural phenotypes from ES cells, but not in neural stem cell self-renewal (Aubert et al., Nat Biotechnol 20:1240-5 (2002)). Glycosylated cystatin C(CCg) has been proposed to be another locally acting agent, which appears to act as a co-factor to potentiate FGF2-activated progenitor cell division, permitting FGF-dependent expansion to operate down to very low cell densities (Taupin et al., Neuron 28:385-397 (2000)). However, although CCg appears to be a promising autocrine/paracrine agent promoting progenitor cell expansion, it acts as a co-factor, and does not operate alone as a self-renewal factor.

The present invention is directed to overcoming these deficiencies in the art.

SUMMARY OF THE INVENTION

The present invention relates to a method of inhibiting differentiation of a population of neural stem cells. This involves providing a purinergic receptor agonist and a population of neural stem cells. The purinergic receptor agonist are then contacted with the population of neural stem cells under conditions effective to inhibit differentiation of the population of neural stem cells.

Another aspect of the present invention relates to a method of producing neurons and/or glial cells from a population of neural stem cells. This involves providing a purinergic receptor antagonist and a population of neural stem cells. The purinergic receptor antagonist is then cultured with the population of neural stem cells under conditions effective to cause the neural stem cells to differentiate into neurons and/or glial cells.

The present invention also relates to a method of inducing proliferation and self-renewal of neural stem cells in a subject. This involves providing a purinergic receptor agonist and administering the purinergic receptor agonist to the subject under conditions effective to induce proliferation and self-renewal of neural stem cells.

A further aspect of the present invention relates to a method of treating a neurological disease or neurodegenerative condition in a subject. This involves providing a purinergic receptor agonist and administering the purinergic receptor agonist to the subject under conditions effective to treat the neurological disease or neurodegenerative condition.

The present invention further relates to a method of treating a neoplastic disease of the brain or spinal cord in a subject. This involves providing a purinergic receptor antagonist and administering the purinergic receptor antagonist to the subject under conditions effective to treat the neoplastic disease of the brain or spinal cord.

Extracellular ATP and ADP, acting through P2Y purinoceptors, act as mitogens for primary neural stem cells. Furthermore, purinergic signaling decreased the density of neural stem cells required for their maintenance and expansion. Importantly, ATP-stimulated neural stem cells remain competent to differentiate into all terminal neural phenotypes at all stages of in vitro expansion, indicating that purines may act as self-renewal factors for neural stem cells. In vitro, this is attended by single cell bursts of point source ATP release, that serve in an autocrine fashion to mediate the expansion of neurospheres. In vivo, purinergic mediation of neural stem cell expansion is manifested by the regionally-restricted expression of purine ectonucleotidase, which generates extracellular ADP, in both the fetal ventricular zone, and in specifically neurogenic regions of the adult brain. Together, these observations indicate that purines act as self-renewal signals for neural stem cells and suggest that the local modulation of extracellular purine availability may regulate neurogenesis from endogenous progenitors in the adult mammalian forebrain.

Neural stem cells are self-renewing multipotential progenitors, that may be maintained in suspension culture as free-floating neurospheres. Neural stem cells typically exhibit a density-dependent survival and expansion, such that critical densities are required below which clonogenic progenitors are lost. This suggests that short-range autocrine factors may be critical for stem cell maintenance. The present examples show that purines drive neural stem cell expansion, and that purine receptor activation is required for stem cells to be maintained as such. Neural progenitors expressed P2Y purinergic receptors and mobilized intracellular calcium in response to an agonist. Receptor antagonists halted division and permitted differentiation into neurons and glia. Real-time bioluminescence imaging of extracellular ATP revealed that the source of extracellular nucleotides are the stem cells themselves which appear to release ATP in episodic burst events. In vivo, enzyme histochemistry of the adult rat brain for ectonucleotidase activity revealed that ATPase sharply and specifically co-localized with persistently neurogenic regions of the brain, including the subventricular zone and the dentate gyrus. On this basis, it is believed that terminal neuronal differentiation is negatively regulated by purine nucleotides which act instead as self-renewal signals for neural stem cells.

BRIEF DESCRIPTION OF THE DRAWINGS

FIGS. 1A-E show that neuronal differentiation is accompanied with loss of purinergic signaling. FIG. 1A shows $Ca^{2+}$ responses of primary cortical neurons at 1 and 11 days in vitro (DIV) to ATP (100 µM) and $K^+$ (60 mM). The cultures were loaded with the calcium indicator fluo-4/am (45 min, 4.6 µM). FIG. 1B shows $Ca^{2+}$ responses to ATP and $K^+$ as a function of DIV. means±SEM. FIG. 1C shows expression of P2Y1, P2Y2, and P2Y4 at 1 DIV. Expression of P2 receptors were lower in MAP2-positive neurons than in MAP2-negative cells. FIG. 1D shows $Ca^{2+}$ responses to ATP and ATP analogs. The potency by which the ATP agonists mobilized intracellular $Ca^{2+}$ stores is compatible with expression of functional P2Y1 (ADP), P2Y2, and P2Y4 (UTP) receptors. FIG. 1E shows ATP release in response to stimulation by UTP (100 µM) and high $K^+$ (60 mM) as a function of DIV. The pseudocolor scale in A is similar to that in FIG. 2B.

FIGS. 2A-D show the persistence of purinergic signaling in neurospheres. FIG. 2A shows immunostaining against P2Y1, P2Y2, and P2Y4 receptors in neural spheres (6 weeks/passage 3. FIG. 2B shows ATP (100 µM) triggered increases in cytosolic $Ca^{2+}$ in a neural sphere (3th passage). Spheres were loaded with fluo-4/am (4.6 µM, 30 min) and imaged by confocal microscopy. FIG. 2C shows bioluminescence imaging of ATP release from neural spheres. Repeated ATP burst release events occurred from spheres maintained in serum-free medium after stimulation, but not from the spheres in cultured in 1% serum overnight (+serum). Representative bioluminescence recordings from several different cultures are shown. The right panel depicts one of the sphere cultures utilized for imaging in phase contrast. FIG. 2D shows serum reduced in a dose-dependent manner unstimulated (baseline) and stimulated ATP release (100 µM UTP). ATP concentrations were measured in samples collected before and after stimulation. *P<0.01, one-way ANOVA, Bonferroni post-hoc test.

FIGS. 3A-D show purinergic signaling sustained the proliferation of neural progenitors. FIG. 3A shows the mitotic index of neural progenitors determined by the BrdU incorporation assay. The effect of ATP, ADP, 2ClATP, 2meSATP, UTP, γSATP, or αβATP upon BrdU incorporation relative to vehicle-treated controls was quantified at: 0 µM (control), 25 µM (a), 50 µM (b), and 100 µM (c) (left panel). Effect of ATP, adenosine, and NECA at; 0 µM (control), 25 µM (a), 50 µM (b), and 100 µM (c). A combination of the adenosine receptor antagonists DPCPX and MRS-1191 were tested at increasing concentration; 0 µM+0 µM (control), 100 µM+5 µM (a), 200 µM+10 µM, and 400 µM+20 µM (middle panel, same y-axis as left panel). Effect on BrdU incorporation of ATP or the ectonuclease inhibitor AMPCP; at 0 µM (control), 25 µM (a), 50 µM (b), and 100 µM (c). Apyrase was tested at: 0 U/ml (control), 10 U/ml (a), 20 U/ml (b), 40 U/ml (c). RB at; 0 µM (control), 10 µM (a), 20 µM (b), 40 µM (c). Suramin at: 0 µM (control), 75 µM (a), 150 µM (b), 300 µM (c). Lines represents 1-order linear regression. Regression coefficients were in the range of 0.89 to 0.99 (right panel). FIGS. 3B-C show suramin and RB increased the minimal plating density required for survival of neural progenitors. At low plating densities, cells cultured in the presence of suramin or RB died by 5 days in vitro *P<0.01, one-way ANOVA, Bonferroni post-hoc test. Right panels display 1-order regression analysis of the data in the left panel. As shown in FIG. 3D, FAC analysis demonstrates an upregulation of the mitotic repressor, P27 in neural progenitor cells exposed to suramin (300 µM) and RB (40 µM). Bivariate distributions (scattergrams) represent DNA content (cell cycle distribution) versus expression of p27 in individual progenitor cells. The percent of p27 positive cells (above the threshold lines) was quantified based on the level of fluorescence of control cells stained with the secondary antibody only (isotypic control). Inserts Neural spheres immunostained against p27. Nuclei are labeled with propidium iodide.

FIGS. 4A-B show purinergic blockade initiated the differentiation of all major neural lineages. Immunostaining revealed that all major lineages were generated from neural stem cells upon suramin-mediated P2Y blockade. Neurospheres were exposed to suramin (100 µM) or RB (40 µM) for 5 to 7 days and then differentiated in 1% serum after plating on laminin. FIG. 4A shows neurons (MAP2, β-tubulin III, Hu), astrocytes (GFAP) and oligodendrocytes (O4) were co-generated following cell cycle exit. (Nuclei stained with Sytox, green). FIG. 4B shows a table summarizing the expression of neuronal and glial markers after 7 days of differentiation in presence of 1% serum. *P<0.01, one-way ANOVA, Bonferroni posthoc test.

FIGS. 5A-E show that ATP ectonucleotidase activity localizes sharply to neurogenic regions of the brain. FIG. 5A shows P2Y receptor expression extended throughout the telencephalic ventricular zone of embryonic brain (E14). FIG. 5B shows P2Y expression was more sharply localized to ependymal and subependymal layer of the adult ventricular wall (P65). FIG. 5C shows ATP ectonucleotidase activity (left) in the adult brain was localized to the striatal ventricular wall, extending dorsolaterally to the take-off of rostral migratory stream (inset). FIG. 5D shows a no-ATP control for the specificity of the ectonucleotidase histochemistry). Lesser degrees of enzyme activity were also noted in the callosal wall. FIG. 5E shows the subgranular zone of the dentate gyrus also exhibited prominent ectonucleotidase activity. The striatal ventricular wall, RMS, and dentate are the only persistently neurogenic regions of the adult brain and were the only regions to exhibit high levels of ectonucleotidase activity.

DETAILED DESCRIPTION OF THE INVENTION

The present invention relates to a method of inhibiting differentiation of a population of neural stem cells. This involves providing a purinergic receptor agonist and a population of neural stem cells. The purinergic receptor agonist is then contacted with the population of neural stem cells under conditions effective to inhibit differentiation of the population of neural stem cells.

The purinergic receptor is a P2Y purinergic receptor.

The purinergic receptor agonist can be adenosine triphosphate, adenosine diphosphate, uridine triphosphate, uridine diphosphate, 2-chloro-adenosine triphosphate, γ-thio-adenosine triphosphate, or 2-methylthio-adenosine triphosphate.

The neural stem cells are mammalian, preferably human.

Another aspect of the present invention relates to a method of producing neurons and/or glial cells from a population of neural stem cells. This involves providing a purinergic receptor antagonist and a population of neural stem cells. The purinergic receptor antagonist is then cultured with the population of neural stem cells under conditions effective to cause the neural stem cells to differentiate into neurons and/or glial cells (i.e. astrocytes and oligodendrocytes).

The purinergic receptor is a P2Y purinergic receptor.

The purinergic receptor antagonist is selected to suppress the release of adenosine triphosphate from neural stem cells. Suitable antagonists are suramin, periodate oxidized adenosine 5'-triphosphate ("Oxidized-ATP"), brilliant blue G ("BBG"), hexamethylene amiloride ("HMA"), diinosine pentaphosphate ("Ip5I"), pyridoxal-5'-phosphate-6-azophenyl-2',5'-disulphonic acid ("isoPPADS"), 1-[N,O-bis(5-isoquinolinesulfonyl)-N-methyl-L-tyrosyl]-4-phenylpiperazine ("KN-62"), pyridoxal-5'-phosphate-6-azophenyl-4'-carboxylate ("MRS 2159"), 8,8'-(carbonylbis(imino-3,1-phenylene carbonylimino)bis(1,3,5-napththalenetrisulfonic acid) ("NF023"), 8,8'-(carbonylbis(imino-4,1-phenylenecarbonylimino-4,1-phenylenecarbonylimino)bis(1,3,5-napththalenetrisulfonic acid) ("NF279"), pyridoxal-5'-phosphate-6-(2'-naphthylazo-6-nitro-4',8'-disulphonate) ("PPNDS"), reactive blue 2 ("RB-2"), 2',3'-O-(2,4,6-trinitrophenyl) adenosine triphosphate ("TNP-ATP"), adenosine 3'-phosphate 5'-phosphosulphate ("A3P5PS"), 2'-deoxy-N-6-methyladenosine-3',5'-bisphosphate ("MRS 2179"), (N)-methanocarba-N-6-methyl-2-chloro-2'-deoxyadenosine-3',5'-bisphosphate ("MRS 2279"), pyridoxal-5'-phosphate-6-azophenyl-2',4'-disulphonic acid ("PPADS"), N6-[2-(methylthio)-ethyl]-2-(3,3,3-trifluoropropyl)thio-5'-adenylic acid ("AR-C69931MX"), N1-(6-ethoxy-1,3-benzothiazol-2-yl-2-(7-ethoxy-4-hydroxy-2,2-dioxo-2H-2-6benzo[4,5][1,3]thiazolo[2,3-c][1,2,4]thiadiazin-3-yl)-2-oxo-1-ethanesulfonamide ("C1330-7"), 2-methylthioadenosine-5'-monophosphate ("2-MeSAMP"), 8-cyclopentyl-1,3-dimethylxanthine ("CPT"), 8-cyclopentyl-1,3-dipropylxanthine ("CPX"), 3-(3-Iodo-4-aminobenzyl)-8-(4-oxyacetate)-phenyl-1-propyl xanthine ("I-ABOPX"), 1,3-diethyl-8-(3,4-dimethoxyphenylethyl)-7-methyl-3,7-dihydro-1H-purine-2,6-dione ("KW 6002"), 3-ethyl 5-benzyl 2-methyl-6-phenyl-4-phenylethynyl-1,4-(±)-dihydropyridine-3,5-dicarboxylate ("MRS 1191"), 2,3-diethyl-4,5-dipropyl-6-phenylpyridine-3-thiocarboxylate-5-carboxylate ("MRS 1523"), 9-chloro-2-(2-furyl)-5-phenylacetylamino[1,2,4]-triazolo[1,5-c]quinazoline ("MRS 1220"), N6-cyclopentyl-9-methyladenine ("N-0840"), N-(2-methoxyphenyl)-N'-(2-(3-pyridyl)quinazolin-4-yl)urea ("VUF 5574"), 8-(N-methylisopropyl)amino-N-(5'-endohydroxy-endonorbornyl)-9-methyladenine ("WRC-0571"), 8-[4-[[[[(2-aminoethyl)amino]carbonyl]methyl] oxy]phenyl]-1,3-dipropylxanthine; xanthine amine congener ("XAC"), 8-[4-[[(4-cyano)phenylcarbamoylmethyl]oxy] phenyl]-1,3-di-(n-propyl)xanthine ("MRS 1754"), 8-(3-chlorostyryl)caffeine, or alloxazine.

The neural stem cells are mammalian, preferably human.

The present invention also relates to a method of inducing proliferation and self-renewal of neural stem cells in a subject. This involves providing a purinergic receptor agonist and administering the purinergic receptor agonist to the subject under conditions effective to induce proliferation and self-renewal of neural stem cells.

The purinergic receptor agonist is as described above and is administered to the subject orally, parenterally, intrathecally, by way of the lateral ventricles, or by way of the ventricular zone wall. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The subject is a mammal, preferably a human.

A further aspect of the present invention relates to a method of treating a neurological disease or neurodegenerative condition in a subject. This involves providing a purinergic receptor agonist and administering the purinergic receptor agonist to the subject under conditions effective to treat the neurological disease or neurodegenerative condition.

The purinergic receptor agonist, its formulation, and modes of administration for this aspect of the present invention are as described above.

The neurological disease or neurodegenerative condition treated by this aspect of the present invention can be Alzheimer's Disease, Huntington's Disease, Parkinson's Disease, amyotrophic lateral sclerosis, multiple sclerosis, stroke, or traumatic injury to the brain and spinal cord.

Again, the subject can be a mammal, preferably a human.

The present invention further relates to a method of treating a neoplastic disease of the brain or spinal cord in a subject. This involves providing a purinergic receptor antagonist and administering the purinergic receptor antagonist to the subject under conditions effective to treat the neoplastic disease of the brain or spinal cord. The purinergic receptor antagonist, its formulation, and modes of administration are described above.

The neoplastic disease of the brain or spinal cord can be neurocytoma, dysplastic neuroepithelial tumor, primitive neuroectodermal tumor, astrocytoma, anaplastic astrocytoma, glioblastoma multiforme, medulloblastoma, neuroblastoma, and ependymoma.

Again, the subject can be a mammal, preferably a human.

EXAMPLES

Example 1

Neuronal Cultures and Neurospheres

Neuronal cultures were prepared from E16 mice and maintained as earlier described (Nedergaard, M., *Science* 263: 1768-1771 (1994), which is hereby incorporated by reference in its entirety). Cytosine arabinoside (20 µM) was added at 48 hr to eliminate proliferating cells. Neural progenitor cells were isolated from E13 mice as previously described (Morshead et al., *Neuron* 13:1071-82 (1994); Reynolds et al., *Science* 255:1707-10 (1992), which are hereby incorporated by reference in their entirety). The forebrains were collected in a Ca/Mg-free Hank's buffered saline solution (HBSS) and dissociated in 0.25% trypsin. The cells were resuspended at $4 \times 10^6$ cells/ml in DMEM/F12/N2 containing 10 ng/ml bFGF and 10 ng/ml EGF (Sigma, St. Louis, Mo.). The cells were plated at 4 ml/dish into 100 mm suspension culture plates and incubated at 37° C. in 5% $CO_2$. The cells were passaged 2 to 3 times before use.

Example 2

Bioluminescence and Calcium Imaging

ATP release from living cells were dynamically imaged by chemiluminescence as described in (Arcuino et al., *Proc Natl Acad Sci USA* 99:9840-5 (2002), which is hereby incorporated by reference in its entirety). Neural spheres were after a light spin resuspended in Ringer's solution and mounted in a temperature controlled Leiden chamber. Luciferase (0.132 mg/ml) and luciferin (0.332 mg/ml) was added to the Ringer solution. After obtaining a baseline recording of 5 minutes duration, the cultures were stimulated by adding an equal volume of $Ca^{2+}$-free Ringer solution containing 100 µM UTP. Light production from the luciferin-luciferase reaction was imaged by a liquid nitrogen-cooled CCD camera (VersArray 1300B, Princeton Instruments), using a 20× oil lens (N.A. 0.8, Olympus), 8×8 binning, and two seconds integration. ATP content in samples collected from cultures grown in 24-well tissue culture plates was measured using a Victor2 plate reader (Wallac) (Cotrina et al., *Proc. Natl. Acad. Sci.* 95:15735-15740 (1998), which is hereby incorporated by reference in its entirety) and normalized to the protein content (BioRad) or to the cell number. A minimum of 8 independent experiments was evaluated ($n \geq 8$, most >20). When drugs or serum were used, the standards were adjusted to containing an equivalent amount.

Example 3

Immunocytochemistry, Enzyme Histochemistry, and Cell Cycle Kinetics

Cultures were stained for nestin (monoclonal clone Rat 401, IgG1, or rabbit antiserum, Chemicon, Temecula, Calif.; 1:2000), neuronal class III β-tubulin (monoclonal clone TuJ1, IgG2a, Covance, Philadelphia, Pa.; 1:500), MAP-2 (2a+2b) (monoclonal clone AP-20, ascites fluid, Sigma, St. Louis, Mo.; 1:500), Neuronal protein HuC/HuD (monoclonal 16A11, Molecular Probes, Eugene, Oreg.; 15 µg/ml), O4 (monoclonal IgM supernatant; O4 hybridoma, or GFAP (mouse clone GA5, or rabbit antiserum, Sigma; 1:500,), purinergic receptors P2Y1, P2Y2, P2Y4 (polyclonal, Alomone Labs, Jerusalem, Israel, 1:200), p27 (polyclonal, Chemicon, 1:2000), cyclins D1 and E (polyclonal, H-295 and M-20, respectively, Santa Cruz Biotechnology, Santa Cruz, Calif.; 1:100), Secondary antibodies were FITC-conjugated goat anti-mouse IgM (µ-chain specific, Sigma; 1:500), Cy3-conjugated goat-anti-rabbit IgG (H+ L) (1:200), Cy5-conjugated Goat-anti-mouse IgG (H+L) (both from Jackson ImmunoResearch, West Grove, Pa.; 1:100). Nuclei were counter-stained with Sytox Green or propidium iodide (Molecular Probes). P27, cyclin D and cyclin E FACS analyses were performed on an EPICS ELITE ESP flow cytometer/cell sorter (Beckman Coulter), as described (Deptala et al., *Int J Oncol* 15:861-71 (1999), which is hereby incorporated by reference in its entirety). The analysis of ectonucleotidase activity was adapted from Braun et al., "Expression of the Ecto-ATPase NTPDase2 in the Germinal Zones of the Developing and Adult Rat Brain," *Eur. J. Neurosci.* 17:1355-64 (2003), which is hereby incorporated by reference in its entirety. Cryostat sections from paraformaldehyde-perfused animals were utilized. All experiments used either inosine diphosphate (IDP), adenosine diphosphate (ADP), or adenosine triphosphate (ATP) as substrate (1 mM), whereas substrate was omitted from controls.

Example 4

Cell Proliferation

For the BrdU incorporation assay, the cultures were incubated for 4 hrs in BrdU (Sigma, 10 µg/ml, 4 hrs), fixed and stained with rat monoclonal anti-BrdU (MAS250C, Harlan Sera-lab, Loughborough, UK; 1:200) and Cy3-conjugated goat anti-rat antibodies (Jackson ImmunoResearch, 1:300). Nuclei were visualized by Sytox (Molecular Probes, Inc.), and the mitotic index was calculated as the ratio of BrdU/Sytox positive nuclei. Limiting dilution analysis was performed as previously described (Keyoung et al., *Nature Biotechnology* 19:843-850 (2001); Uchida et al., *Proc. Natl.*

Acad. Sci. 97:14720-14725 (2000), which are hereby incorporated by reference in their entirety).

Example 5

Purines Act as Mitogens for Primary Neural Precursor Cells

To test the idea that purinergic signaling is restricted to undifferentiated neural precursor cells, $Ca^{2+}$ responses to ATP were first examined as a function of time after plating either neural stem cells or differentiated neurons. Cultured mouse cortical neurons in near-pure neuronal cultures were loaded with fluo-4/am and exposed to either ATP (100 µM) or $K^+$ (60 mM). Transient increments in $Ca^{2+}$ were triggered by ATP, but not by high $K^+$, in cultures younger than 2 days in vitro (DIV) (FIG. 1A). The responses to ATP fell by day 3 and were absent 9 days after plating. In contrast, the maturing neurons gained sensitivity to $K^+$ by day 3 and exhibited a many-fold increase in cytosolic $Ca^{2+}$ in response to high mM $K^+$ from day 9 (FIG. 1B). Immunostaining revealed that the P2Y1, P2Y2, and P2Y4, and purinergic receptors were abundantly expressed by nestin$^+$ progenitor cells, but the expression of each fell with neuronal maturation (FIG. 1C). By 30 hours after plating, MAP2-defined neurons expressed substantially less P2Y receptor-immunoreactivity than did neighboring, MAP2$^-$ cells (FIG. 1C). By 5 days, P2Y-immunoreactivity was restricted to GFAP$^+$ astrocytes.

The ATP-induced increase in $Ca^{2+}i$ in 1-2 day cultures was concentration-dependent, with an $IC_{50}$ of 8.8±1.5 µM. ATP-induced $Ca^{2+}_i$ increments were inhibited by both suramin (100 µM) and reactive blue (RB; 30 µM), two mechanistically-unrelated inhibitors of purinergic signaling (FIG. 1D). A variety of purine receptor agonists, that included ATP, ADP, UTP, 2-Cl-ATP, γSATP, and 2-MeSATP, increased $Ca^{2+}_i$ with roughly equal potency. Removal of extracellular $Ca^{2+}_i$ did not significantly decrease the response to ATP or 2-MesATP. Taken together, these results suggest that ATP primarily mobilized intracellular $Ca^{2+}$ stores, rather than opening $Ca^{2+}$ permeable channels in neural progenitor cells. Consistent with this notion, αβATP—a P2X specific agonist, failed to evoke $Ca^{2+}$ responses, while oxidized ATP (300 µM, 1 hr, a P2X7 antagonist) did not significantly reduce ATP-evoked $Ca^{2+}$ responses (p=0.4, Student's t test).

Example 6

Purines are Released as Autocrine Factors and Signal Through P2Y Receptors

The postulate that neural stem and progenitor cells might secrete purine nucleotides, thereby allowing nucleotides to promote proliferation through an autocrine/paracrine signaling pathway, was next tested. It was found that purine receptor activation by UTP (a P2Y agonist, with a potency similar to that of ATP) evoked robust ATP release by neuroepithelial cells during their first 2 days in vitro, but not in more differentiated cultures (FIG. 1E) (Cotrina et al., *Proc. Natl. Acad. Sci.* 95:15735-15740 (1998); Cotrina et al., *J Neurosci* 18:8794-804 (1998), which are hereby incorporated by reference in their entirety). Importantly, high potassium failed to elicit ATP release from mature neurons, despite triggering robust increases in cytosolic calcium. Thus, neurons lose their ability to release ATP in response to elevations of $Ca^{2+}_i$, concomitant with their down-regulation of P2Y receptors (FIG. 1E). In contrast, if the same cells were cultured as free floating neurospheres, the uncommitted nestin$^+$ progenitor cells continued to express P2Y receptor-immunorecativity (FIG. 2A) and to respond to purine agonists with sustained increments in cytosolic $Ca^{2+}$ after repetitive passage (FIG. 2B).

Purinergic receptors are characterized by rapid and sustained desensitization in response to agonist exposure and transient repeated episodes of agonist exposures are more efficient than chronic stimulation. To address the question of the source and mechanism of ATP release, the pattern of ATP release from neural spheres was visualized using bioluminescence imaging. Specifically, a mixture containing luciferase and its substrate, luciferin, were added to the culture medium. By this approach, ATP release can be monitored by light emissions resulting from the ATP-triggered luciferase breakdown of luciferin, both at the single-cell level and in real time, using a liquid nitrogen-cooled CCD camera (FIG. 2C) (Arcuino et al., *Proc Natl Acad Sci USA* 99:9840-5 (2002), which is hereby incorporated by reference in its entirety). At baseline, the majority of the neural spheres exhibited little photo-detectable ATP release. In contrast, stimulation with UTP (100 µM) resulted in frequent point-source bursts of light emission. These ATP bursts were variable in their duration and extent of spatial expansion but were abrupt in onset and spherical in their spread, likely reflecting ATP diffusion from a point-source (Arcuino et al., *Proc Natl Acad Sci USA* 99:9840-5 (2002), which is hereby incorporated by reference in its entirety).

Example 7

Effects were Signaled Through ATP/ADP-dependent P2Y Activation

Purinergic signaling has long-term effects on proliferation of numerous cell types, including rapidly replicating transformed cell lines (Burnstock, G., *Arterioscler Thromb Vasc Biol* 22:364-73 (2002); Michoud et al., *Am J Respir Cell Mol Biol* 27:732-8 (2002); Sauer et al., *J Cell Sci* 115:3265-73 (2002); Tu et al., *Br J Pharmacol* 129:1481-9 (2000), which are hereby incorporated by reference in their entirety). To better define the mitogenic effects of P2Y on neural progenitor cells, the mitogenic effects of ATP, its analogs, and its dephosphorylated metabolites were compared. To this end, BrdU incorporation by neural stem cells was quantified after 4 hrs incubation in each treatment. ATP increased proliferation in a dose-dependent manner, peaking at 100 µM. Several ATP analogs, including ADP, ATPγS, 2Cl-ATP, and UTP, had comparable effects, with the exception that the P2X agonist αβATP (FIG. 3A, left panel). The mitogenic action of nucleotides was not a result of hydrolysis of ATP to adenosine, because ATPγS is non-degradable and because adenosine and NECA (an A1 and A2 adenosine agonist) failed to stimulate proliferation. A combination of adenosine receptor antagonists DPCPX and MRS 1191 was also without effect, suggesting that P1 receptors do not contribute to the mitogenic action of ATP (FIG. 3A, middle panel). In support of a key role of ATP and ADP signaling through P2Y receptors, the ectonucleotidase inhibitor α,β-methyl adenosine diphosphate (AMPCP), which blocks the breakdown of ATP and ADP to AMP, potently enhanced the mitotic expansion of neural progenitors. In contrast, the ATPase apyrase, which hydrolyses ATP and ADP to AMP, inhibited proliferation. In addition, the two P2Y receptor antagonists, suramin and RB (RB), inhibited proliferation in a dose-dependent manner (FIG. 3A, right panel).

Example 8

Purinergic Blockade Increased the Cell Densities Required for Neurosphere Expansion and Survival To assess the requirement of P2Y signaling in self-renewal, neurospheres were dissociated to low density cultures and limiting dilution analysis performed, in the presence or absence of either suramin or RB. Both suramin and RB increased the minimum density at which the cells could remain viable and expand (FIGS. 3B-C). Thus, purinergic receptor activation was required not only for continued proliferation of neural progenitors, but also for survival at low plating densities. This suggested that purinergic receptor activation decreased the density of cells required for the expansion and survival of neurospheres, as would be expected of a mitogen that supported self-renewing divisions.

Example 9

Purinergic Inhibition Decreased the Mitotic Index of Neural Stem Cells

Flow cytometry confirmed that the purinergic inhibitors decreased the fraction of cells in S phase: 16.4%±1.8% of cells acutely dissociated from untreated control neurospheres were in S-phase, compared to 5.7±0.3% and 8.4±2.3 in RB and suramin treated cultures, respectively (p<0.001) (Deptala et al., *Int J Oncol* 15:861-71 (1999), which is hereby incorporated by reference in its entirety). The inhibition of proliferation afforded by suramin and RB was reversible. The percentage of cells in S-phase recovered by 50% at 8 h and by 80% at 24 hr after wash-out of the drugs. Suramin-treated cultures also exhibited an increase in the tumor suppressor P27, a strong negative regulator of cell division. P27 expression rose more strongly in RB—than suramin-treated cultures, in accord with the stronger inhibition of cell proliferation afforded by RB (FIG. 3D).

Example 10

Purinergic Blockade Did not Affect Phenotypic Differentiation

The lineage potential of progenitors whose division was suppressed by suramin or RB was examined by clonal expansion. In brief, neural spheres rendered mitotically quiescent by 5 day exposure to suramin and RB were dissociated and plated at low density in fresh medium without inhibitors. Seven days later, the cultures were fixed and immunostained for a panel of lineage-associated markers. Immediately after plating, both sets of cultures strongly expressed nestin, a marker of immature precursors. After 7 days in culture, a significant number of the cells had differentiated into neurons, astrocytes, and oligodendrocytes (<1-3%) (FIG. 4A). Importantly, neither suramin nor RB restricted the lineage potential of exposed progenitor cells. After re-expansion, the antagonist-treated cultures contained neurons, astrocytes, and oligodendrocytes, and in the same relative proportions as their untreated controls (FIG. 4B). These results indicated that the suppression of stem cell expansion induced by RB and suramin did not influence the differentiation paths available to the progeny of those cells.

Example 11

Ectonucleotidase Activity was Associated with Undifferentiated Cells

Ectonucleotidases are extracellular ATP hydrolyzing enzymes, that modulate purinergic signaling by rapidly degrading ATP. Initial ectonucleotidase breakdown of ATP provides ADP, a strong agonist of P2Y receptor activation, while further breakdown to AMP, a poor agonist for P2Y receptors, may act as a brake on P2Y signaling. As a result, areas of P2Y signaling are characterized by intense ectonucleotidase activity. On this basis, enzyme histochemical analysis was used to assess ectonucleotidase activity both in vitro and in vivo. In culture, neurospheres exhibited both intense and uniform staining when using either ATP or ADP as a substrate for lead-deposition ectonucleotidase histochemistry. Plating of the neurospheres or exposure to serum each resulted in rapid and sharp decreases in staining intensity. Thus, uncommitted progenitor cells were characterized not only by a high level of P2Y receptor expression and spontaneous ATP release, but also by high level of endogenous ectonucleotidase activity, that served to provide local ADP as bioactive agonist. During neural differentiation, P2Y receptor expression fell, both ATP release and ATP-triggered cytosolic $Ca^{2+}$ mobilization were attenuated. These events were attended by a fall in ectonucleotidase activity and consequent drop in available agonist.

Example 12

P2Y Receptors and Ectonucleotidase Activity Localized to Neurogenic Regions of Brain To assess the involvement of ATP/P2Y receptor signaling in neural differentiation in vivo, the expression of P2Y receptors and ectonucleotidase activity in both fetal (E14) and adult rat brain was analyzed (FIG. 5A). In the fetal brain, the receptor density appeared evenly distributed across the developing cortex, whereas a relative higher abundance of P2Y receptor expression was evident in the subventricular zone of adult animals. Similar pattern of expression of P2Y1 and P2Y4 receptors were observed.

Enzyme histochemical analysis of ectonuclease activity was next utilized to map ectonuclease activity in brain sections (FIGS. 5B-C). The enzyme reaction was performed on cryostat sections incubated in either ATP or ADP as substrate. The analysis revealed a striking pattern of high enzyme activity corresponding to neurogenic areas in adult brain. In the ventricular wall, high enzyme activity was evident in the subependymal zone, especially along the striatal wall and its rostrolateral tip, from which arises the highly neurogenic rostral migratory stream. In addition, the subgranular zone ("SGZ") of the hippocampus, a neurogenic zone that gives rise to new dentate granule neurons, expressed high ectonucleotidase activity, again with striking anatomic specificity (FIG. 5).

These experiments revealed that ATP can act as an autocrine factor for the replication and self-renewal of neural stem cells. It was found that when maintained as mitotically-active neurospheres, neural progenitor cells exhibited both ATP release and purinergic receptor-activated calcium mobilization. Real-time bioluminescence imaging of ATP release revealed that the stem cells themselves were the source of ATP, which they released in brief burst events. External addition of ATP or its analogs increased the mitotic index and rate of neural progenitor cells, whereas P2Y antagonists suppressed both neurosphere expansion and the mitotic index of cells within those spheres. Both ATP release and purine-activated calcium responses were retained over several months of repetitive passage, as was the reversible suppression of neurosphere expansion by P2Y antagonists. Strikingly, both the mitotic competence and multilineage potential of the cultured neural stem cells were restored upon P2Y antagonist removal. This is in marked contrast to the expansion associated with other described positive regulators of neural stem cell expansion, such as sonic hedgehog, which have typically been associated with a sustained loss of neuronal differentiation competence (Wechsler-Reya et al., *Neuron* 22:103-14 (1999), which is hereby incorporated by reference in its entirety).

The relative fractions of neurons, astrocytes, and oligodendrocytes that developed after plating of neurospheres were essentially unchanged in controls versus antagonist treated cultures. Using real-time bioluminescence imaging of ATP release, it was demonstrated that ATP was released by individual cells within each neurosphere in brief, almost evanescent bursts, that were exhibited by only a minor fraction of the cells. Because purinergic receptors exhibit rapid desensitization to sustained agonist exposure, such brief bursts of transmitter release might better stimulate proliferation than a more sustained stimulus, to which the cells might quickly become refractory (Burnstock, G., *Clin Med* 2:45-53(2002), which is hereby incorporated by reference in its entirety).

Interestingly, such point-source bursts of ATP have been previously identified in cultured astrocytes, where they appear linked to the opening of anion channels, and hence to the channel-mediated efflux of cytosolic ATP (Arcuino et al., *Proc Natl Acad Sci USA* 99:9840-5 (2002), which is hereby incorporated by reference in its entirety). This may suggest a role for purinergic signaling in the functional maintenance of the astrocytic syncytium. In addition, astrocytes have been implicated in the support of neurogenesis from progenitor cells in neurogenic regions of the adult brain (Lim et al., *Neuron* 28, 713-726 (2000) and Gage, F., *Science* 287:1433-1438 (2000), which are hereby incorporated by reference in their entirety). Acting in concert with progenitor-derived ATP, the paracrine activation of neural stem cells by their astrocytic neighbors might then serve to maintain their undifferentiated self-renewal. As such, astrocytic ATP may be viewed as negatively regulating neurogenesis, by maintaining the self-renewal of resident precursors while suppressing their terminal neuronal or glial differentiation.

In accord with this model, both serum exposure and substrate anchorage substantially reduced the ability of neural progenitors to release ATP, consistent with the differentiative effects of both serum and substrate on neural progenitor cells (Goldman et al., *J. Neurosci.* 12:2532-41 (1992) and Reynolds et al., *Science* 255:1707-10 (1992), which are hereby incorporated by reference in their entirety). Indeed, nucleotide-mediated signaling was rapidly lost during neuronal differentiation: Purinergic receptor expression was uniformly down-regulated early in the process of neuronal differentiation, and exposure to receptor agonists failed to mobilize cytosolic calcium in MAP-2$^+$ neurons. Together, these observations suggest that neural stem cells both release ATP and respond to it with mitotic expansion. As such, ATP appears to act through both autocrine and paracrine routes to regulate the mitotic expansion and self-renewal of neural stem cells. The high ectonucleotidase activity of cultured neurospheres may serve to modulate this process by regulating ATP and ADP bioavalability, while independently suggesting that expanding neural stem and progenitor cells actively engage in purinergic signaling.

ATP release and purinergic signaling may be critical not only to developmental stem cells expansion and neurogenesis but also to the self-renewal and expansion of persistent stem and progenitor cells of the adult brain. Indeed, on the basis of the above observations, it would be predicted that the maintenance of purinergic signaling shall prove required for persistent neurogenesis in neurogenic regions of the adult brain. This possibility is independently supported by the sharp and specific localization of ectonucleotidase activity to the neurogenic regions of the adult brain, in particular to the striatal subependyma, rostral migratory stream and subgranular zone of the dentate gyrus. This pattern clearly suggests the necessity of purinergic signaling to both progenitor expansion and adult neurogenesis.

The localization of both P2Y receptors and ectonucleotidase activity to regions of active mitotic stem cell expansion and neurogenesis in vivo is especially significant given the demonstration that P2Y-activated purinergic signaling, including that triggered by ATP burst release, may be required for neural stem cell self-renewal in vitro. Indeed, the structure of this autocrine/paracrine pathway suggests that it may constitute a critical regulatory checkpoint for lineage commitment by neural stem cells. As such, its abrogation, through a suppression of either purine release or reception, may comprise a means of inhibiting undesired stem or progenitor cell expansion, as may be the case in neoplasias of the CNS. In contrast, its stimulation may provide a means of expanding progenitor cell populations, to provide an expanded cellular substrate for strategies designed to induce neurogenesis from endogenous progenitor cell pools. On this basis, the pharmacological regulation of purinergic signaling may permit a means of modulating neurogenesis in both the fetal and adult brain.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of producing neurons and/or glial cells from neurospheres grown from mammalian neural stem cells in cell culture, said method comprising:
    exposing said neurospheres to an effective amount of a P2Y1, P2Y2, and P2Y4 purinergic receptor antagonist until said neurospheres are rendered mitotically quiescent; and
    plating said neurospheres in cell culture medium in the absence of said antagonist, said cell culture medium sufficient to differentiate the plated neurospheres into neurons and/or glial cells.

2. The method according to claim 1, wherein the purinergic receptor antagonist is selected from the group consisting of suramin, periodate oxidized adenosine 5'-triphosphate ("Oxidized-ATP"), reactive blue 2 ("RB-2"), adenosine 3'-phosphate 5'-phosphosulphate ("A3P5PS"), 2'-deoxy-N6-methyladenosine-3',5'-bisphosphate ("MRS 2179"), (N)-methanocarba-N6-methyl-2-chloro-2'-deoxyadenosine-3', 5'-bisphosphate ("MRS 2279"), and pyridoxal-5'-phosphate-6-azophenyl-2',4'-disulphonic acid ("PPADS").

3. The method according to claim 1, wherein the neural stem cells are human.

4. The method according to claim 1, wherein the glial cells are astrocytes.

5. The method according to claim 1, wherein the glial cells are oligodendrocytes.

* * * * *